United States Patent
Katzlinger et al.

(10) Patent No.: US 7,113,285 B2
(45) Date of Patent: Sep. 26, 2006

(54) MULTIMODE READER

(75) Inventors: Michael Katzlinger, Wals (AT); Joseph Atzler, Wals (AT); Sami D. Alaruri, Indianapolis, IN (US)

(73) Assignee: Beckman Coulter, Inc., Fullerton, CA (US)

( * ) Notice: Subject to any disclaimer, the term of this patent is extended or adjusted under 35 U.S.C. 154(b) by 364 days.

(21) Appl. No.: 10/732,797

(22) Filed: Dec. 9, 2003

(65) Prior Publication Data

US 2005/0122521 A1   Jun. 9, 2005

(51) Int. Cl.
G01N 21/00 (2006.01)
(52) U.S. Cl. .................................................. 356/432
(58) Field of Classification Search .................. None
See application file for complete search history.

(56) References Cited

U.S. PATENT DOCUMENTS

| | | | | |
|---|---|---|---|---|
| 4,573,073 | A * | 2/1986 | Corby, Jr. ................... | 348/26 |
| 4,817,119 | A * | 3/1989 | Ledley et al. ................. | 378/9 |
| 5,565,360 | A | 10/1996 | Lapota et al. ............. | 435/286.7 |
| 5,784,152 | A | 7/1998 | Heffelfinger et al. ......... | 356/73 |
| 5,959,738 | A | 9/1999 | Hafeman et al. ........... | 356/440 |
| 6,043,880 | A | 3/2000 | Andrews et al. ........... | 356/311 |
| 6,084,680 | A | 7/2000 | Tuunanen et al. .......... | 356/417 |
| 6,317,207 | B1 | 11/2001 | French et al. .............. | 356/317 |
| 6,326,605 | B1 | 12/2001 | Modlin et al. .............. | 250/214 |
| 6,455,861 | B1 | 9/2002 | Hoyt ....................... | 250/458.1 |
| 6,476,907 | B1 | 11/2002 | Gordon ..................... | 356/73 |
| 6,498,335 | B1 | 12/2002 | Modlin et al. .............. | 250/214 |
| 6,512,580 | B1 | 1/2003 | Behringer et al. .......... | 356/244 |
| 6,597,450 | B1 | 7/2003 | Andrews et al. ........... | 356/317 |
| 6,832,849 | B1 * | 12/2004 | Yoneda et al. .............. | 362/551 |
| 6,903,738 | B1 * | 6/2005 | Pfister et al. ............... | 345/420 |
| 2001/0007496 | A1 | 7/2001 | Modlin et al. ............... | 356/73 |
| 2001/0019409 | A1 | 9/2001 | French et al. ............... | 356/317 |
| 2001/0033381 | A1 | 10/2001 | Stumbo et al. ............. | 356/440 |
| 2001/0052978 | A1 * | 12/2001 | Lewis et al. ................ | 356/326 |
| 2002/0008871 | A1 | 1/2002 | Poustka et al. ............. | 356/317 |
| 2002/0060791 | A1 | 5/2002 | Stumbo et al. ............. | 356/317 |
| 2002/0109100 | A1 | 8/2002 | Jackson, III et al. ..... | 250/458.1 |
| 2002/0158211 | A1 | 10/2002 | Gillispie ................... | 250/458.1 |
| 2002/0182111 | A1 | 12/2002 | Feygin ..................... | 422/82.05 |
| 2003/0016352 | A1 | 1/2003 | Goldman et al. ........... | 356/317 |
| 2003/0044967 | A1 | 3/2003 | Heffelfinger et al. ..... | 435/287.2 |

(Continued)

FOREIGN PATENT DOCUMENTS

AT   410375 B   4/2003

(Continued)

OTHER PUBLICATIONS

Herman, P., "Frequency-domain fluorescence microscopy with the LED as a light source," *Journal of Microscopy*, 203(2):176-181 (Aug. 2001).

(Continued)

*Primary Examiner*—Michael P. Stafira
(74) *Attorney, Agent, or Firm*—Marc Karish; Sheldon & Mak PC

(57) ABSTRACT

An apparatus for analyzing a plurality of samples in sample sites on a substrate, the apparatus having an array of spaced apart light sources coupled to a moveable support so that one or more of the light sources can be selectively used; a frame for supporting the substrate; a detector configured to detect light; an optical relay configured to transmit light from at least one of the plurality of light sources to a sample site and from the sample site to the detector; and a support structure for supporting the frame, the detector and the optical relay.

20 Claims, 6 Drawing Sheets

U.S. PATENT DOCUMENTS

2004/0065833 A1* 4/2004 Torgrip et al. ............ 250/341.7

FOREIGN PATENT DOCUMENTS

| EP | 0886 136 | 12/1998 |
|---|---|---|
| WO | WO 82/00356 | 2/1982 |
| WO | WO 01/35079 | 5/2001 |
| WO | WO 02/095371 | 11/2002 |

OTHER PUBLICATIONS

Specification Sheet, "GENios Pro—the Injector Reader," Tecan.

Specification Sheet, "CytoFluor® 4000 Fluorescence Multi-Well Plate Reader," AB Applied Biosystems, Foster City, California.

Brochure, "Ultra Evolution Your total solution for Assay Development and High Throughput Screening," Tecan.

Brochure, "Anthos lucy3 Technical Data," Anthos-Labtec Instruments, Salzburg, Austria.

Brochure, "SpectraMex® M2 microplate reader," Molecular Devices Corporation, Sunnyvale, California.

* cited by examiner

MULTIMODE READER

BACKGROUND

The present invention relates to a multimode fluorescence reader.

Optical spectroscopy is the study of the interaction of light with matter. Typically, optical spectroscopy involves monitoring some property of light that is changed by its interaction with matter, and then using that change to characterize the components and properties of a molecular system. Optical spectroscopy is a broad term that describes a number of methods, such as absorption, luminescence (such as photoluminescence and chemiluminescence), and scattering/reflectance, among others. Typically, researchers are interested in conducting numerous different types of analysis, depending on the sample and the properties being researched.

Flexibility in experimental protocols has led to the development of machines that provide top illumination and top detection, top illumination and bottom detection, and bottom illumination and bottom detection. Same-side illumination and detection is typically used for photoluminescence and scattering assays. Opposite-side illumination and detection is typically used for absorbance assays.

Machines having all of the above measurement functionality are often expensive to build and large in size. Moreover, switching between experimental protocols is often time consuming.

Additionally, multiplexing has led to the use of multiple different dyes in samples. The different dyes often require different excitation light sources for detection. Typically, the light sources available with a given detection apparatus are limited.

Examples of attempts to develop machines capable of utilizing more than one type of optical spectroscopy are described in U.S. Pat. No. 5,784,152 to Heffelfinger et al.; U.S. Pat. No. 6,317,207 to French et al.; U.S. Pat. No. 6,326,605 to Modlin et al.; and U.S. Pat. No. 6,498,335 to Modlin et al. However, each of these devices has one or more major disadvantages.

There is therefore a need for a detection apparatus that solves the shortcomings of the prior art.

SUMMARY

The present invention is directed to a multi-mode detection apparatus for analyzing a plurality of samples in sample sites on a substrate. According to an embodiment, the apparatus has an array of spaced apart light sources coupled to a moveable support so that one or more of the light sources can be selectively used; a frame for supporting the substrate; a detector configured to detect light; and an optical relay configured to transmit light from at least one light source to one of the plurality of sample sites and from the sample site to the detector. The apparatus also has a support structure for supporting the frame, the detector and the optical relay.

Optionally, the moveable support is a rotatable wheel. Several LED lamps may be positioned on the rotatable wheel. Optionally, the rotatable wheel has an aperture for the passage of light from an exterior light source not positioned on the wheel. The exterior light source may be a deuterium lamp.

Another aspect of the invention, which can be used with or without the array of light sources, is that the optical relay can be provided with a beam splitter for splitting light from at least one light source into two beams, a first beam being directed to an upper surface of one of the plurality of sample sites, and a second beam directed to a lower surface of one of the plurality of sample sites. The apparatus may have a first shutter selectively moveable to prevent light from the beam splitter from reaching the upper surface of the sample site. The apparatus may have a second shutter selectively moveable to prevent light from the beam splitter from reaching the lower surface of the sample site.

The present invention is also directed to a method for analyzing a sample. A sample is placed at a sample site on the substrate. An excitation light source is selected and emitted light from the sample is then detected.

BRIEF DESCRIPTION OF THE DRAWINGS

A better understanding of the present invention will be had with reference to the accompanying drawings in which.

DETAILED DESCRIPTION

Figure 1:
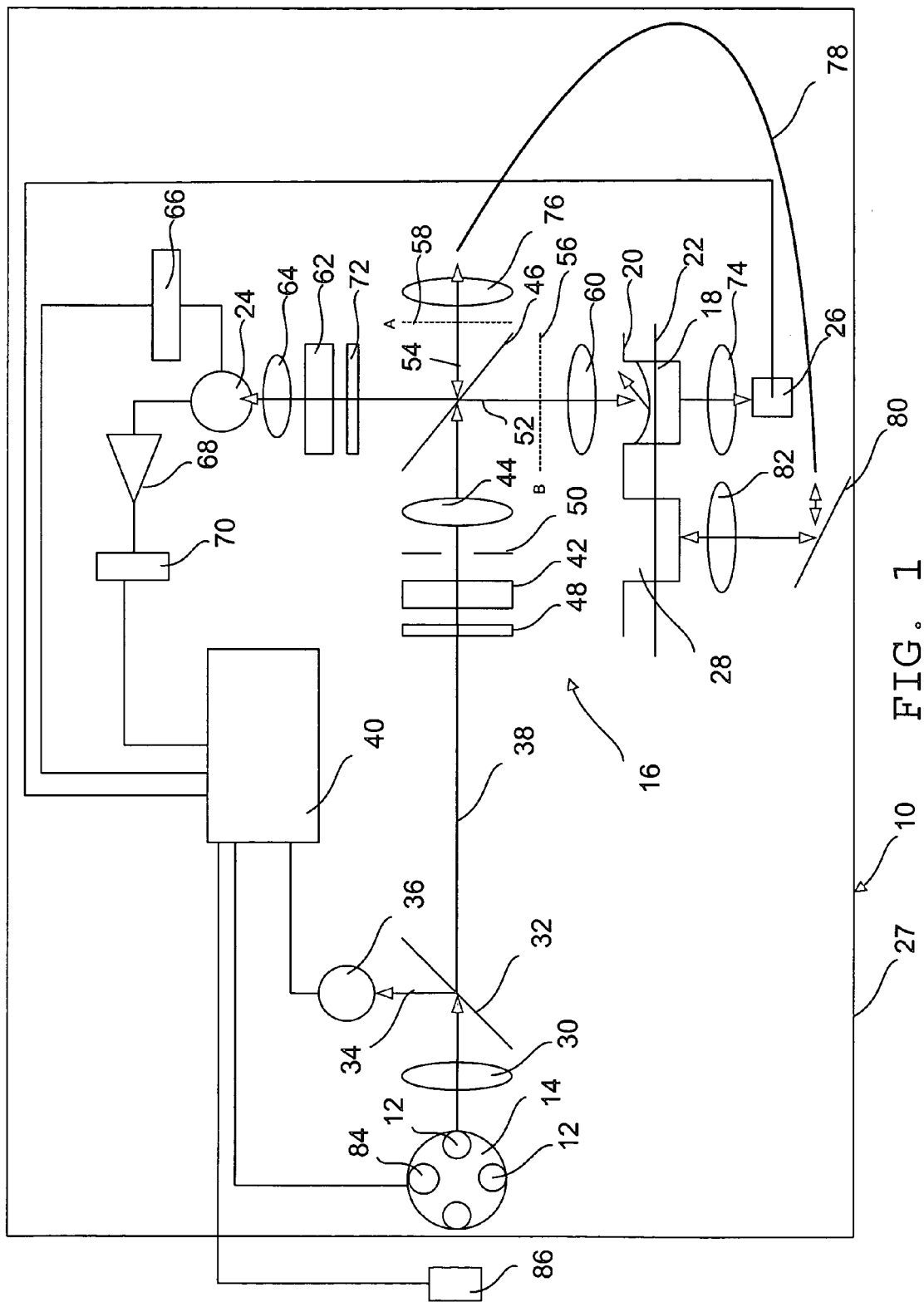
FIG. 1 is a schematic illustration of the components of a detection apparatus according to an embodiment of the present invention.

FIG. 1 shows an apparatus 10 for analyzing samples constructed in accordance with an embodiment of the present invention. The apparatus 10 includes an array of light sources 12, coupled to a moveable support 14 so that one or more of the light sources 12 can be selectively used. Excitation light from the selected light source 12 is conveyed through an optical relay 16 to a sample 18 on a substrate 20 held in a frame 22. Emission light from the sample 18 is either conveyed through the optical relay 16 to an upper detector 24 or passed through the sample to a lower detector 26. A support structure 27 supports the moveable support 14, the frame 22, the optical relay 16, the upper detector 24, and the lower detector 26.

The optical relay 16 shown in FIG. 1 is selectively configurable depending on the type of measurement being performed. As will be seen in FIGS. 2 to 6, some of the components illustrated in the optical relay 16 of FIG. 1 are not used for obtaining some types of measurements. Also, as will be understood by those skilled in the art, additional elements, such as lenses, apertures, and mirrors may be used to further manipulate excitation and emission light.

The substrate 22 may have a plurality of sample sites 28, such as a microplate with associated microplate wells. The optical relay 16 can contain such light handling devices as mirrors, lenses, filters, apertures, and beam splitters. Suitable substrates, light sources, detectors, and optical relay structures for directing light from the light sources to the substrate and from the substrate to the detectors are described below.

Optionally, the detection device 10 also includes a scanning mechanism (not shown) configured to scan the substrate, so that device 10 may read from a plurality of sample sites on the substrate. The scanning mechanism improves read time by reducing the time that the detection optics spends over areas of the substrate that do not contain sample to be interrogated. The scanning mechanism also improves read time because the substrate moves continuously, more rapidly bringing new sample sites on the substrate into position for reading, and because the need for a waiting period for vibrations to subside is reduced or eliminated if the substrate does not jostle the samples by starting, stopping, or otherwise significantly changing speed.

Considering the optical relay 16 in more detail, as shown in FIG. 1, light is directed from the selected excitation light source 12 through a beam collimating (e.g., convex-plano) lens 30 and onto a first beam splitter 32. The first beam splitter 32 directs a first beam of excitation light 34 toward a light monitor 36 and a second beam of excitation light 38 toward the substrate 22. The light monitor 36 is coupled to a control circuit and power supply 40. The control circuit and power supply 40 alters the power to the light source 12 depending on the light detected by the light monitor 36.

The control circuit and power supply 40 is used to correct for fluctuations in the intensity of light provided by the light sources. Such corrections may be performed by reporting detected intensities as a ratio over the luminescence intensity measured by the upper detector 24 to the excitation light intensity measured by the light monitor 36. The light monitor 36 also can be programmed to alert the user if the selected excitation light source 12 fails. A preferred light monitor 36 is a silicon photodiode with a quartz window for low autoluminescence.

The second beam of light 38 is directed through an excitation filter 42, and a lens 44, and onto a second beam splitter 46. The second beam splitter 46 can be a 50/50 fused silica beam splitter. Optionally, if fluorescence polarization is being performed, the second beam of light may also be directed through an excitation polarizer filter 48. Optionally, if a small sample area is to be analyzed, then the second beam of light 38 may be passed through an aperture 50 to limit the diameter of the beam.

The second beam splitter 46, splits the second beam of light into a third beam of excitation light 52 directed toward a top surface of a sample 18 at a sample site 28 on the substrate 20, and a fourth beam of excitation light 54 directed toward a bottom surface of a sample 18 at a sample site 28 on the substrate 20. A first moveable shutter 56 is located in the path of the third beam of excitation light 52 for selectively preventing the third beam of excitation light 52 from reaching the top surface of the substrate 20. A second moveable shutter 58 is located in the path of the fourth beam of excitation light for selectively preventing the fourth beam of light 54 from reaching the bottom surface of the substrate 20. As used herein, the term shutter refers to any means for selectively blocking a beam of light. In an embodiment, the shutters are moveable slats of anodized metal, such as steel.

If not blocked by the first moveable shutter 56, the third beam of excitation light 52 passes through a lens 60, and onto the top of a sample 18 at a sample site 28 on the substrate 20. Optionally, the lens 60 is a quartz, short focal length lens. Optionally, the lens 60 is a liquid lens, the focal length being adjusted by adjusting the current across electrodes of the liquid lens. The third beam of excitation light 52 is used for measuring, for example, fluorescence top intensity, time resolved fluorescence, fluorescence polarization, and absorbance.

Emission light from the top of the sample 18 passes through the lens 60, through the second beam splitter 46, through an emission filter 62, through a collimation lens 64 and onto the upper detector 24. The upper detector 24 is coupled to a power supply 66 and to an amplifier 68. The amplified signal from the detector 24 is transmitted to a photocounting circuit 70 coupled to the control circuit and power supply 40. Optionally, if fluorescence polarization is being performed, the emission light may also be directed through an emission polarizer filter 72.

In the case of absorbance measurement, the third beam of excitation light 52 is transmitted to the top of a sample 18 at a sample site 28 on the substrate 20. Non-absorbed light passes through the sample 18 onto the lower detector 26 positioned below the substrate 20. The lower detector 26 is coupled to the control circuit and power supply 40. The lower detector 26 can be a photodiode.

If not blocked by the second shutter 58, the fourth beam of excitation light 54 passes through a collection/coupling lens 76 and into a fiber optic cable 78. The fiber optic cable 78 directs the fourth beam of light 54 onto a mirror 80. The mirror 80 directs the fourth beam of excitation light through a collection/coupling lens 82 and onto the bottom of a sample 18 at a sample site 28 on the substrate 20.

Light emitted out of the bottom of the sample 18 in response to the fourth excitation light beam 54 passes through the collection/coupling lens 82, and onto the mirror 80. The mirror 80 directs the emitted light through the fiber optic cable 78. The emitted light then passes out of the fiber optic cable 78, through the collection/coupling lens 76 and onto the second beam splitter 46. The second beam splitter 46 directs a portion of the emitted light up through the emission filter 62, through the collimation lens 64 and onto the upper detector 24. The fourth beam of excitation light 54 is used for measuring, for example, bottom fluorescence intensity.

In an additional embodiment of the present invention, the fourth beam of light is blocked, not by the second shutter 58, but by moving the collection/coupling lens 76 and one end of the fiber optic cable 78 out of path of the fourth excitation light beam 54. The collection/coupling lens 76 and one of the fiber optic cable 78 are mounted on a moveable stage (not shown). When the use of the fourth beam of excitation light 54 is desired, the moveable stage is moved to place the collection/coupling lens 76 and one end of the fiber optic cable 78 into the path of the fourth beam of excitation light. The moveable stage may be motorized and computer controlled.

As used herein, the term "light" refers to both visible light and other types of radiation, such as ultraviolet and infrared radiation. The device may be used with any light source, such as arc lamps, incandescent lamps, fluorescent lamps, electroluminescent devices, lasers, laser diodes, and light-emitting diodes (LEDs), among others. In a preferred embodiment, several different wavelength LEDs are mounted to a rotatable wheel used as the moveable support 14. Optionally, to allow a wide spectral range selection for excitation wavelengths, a white LED (450–705 nm) and a set of LEDs with emission wavelengths centered at 370, 430, 470, 590, and 620, 910 and 960 nm are placed on the rotatable wheel. Optionally, the rotatable wheel contains an aperture 84 for passage of light from a light source 86 not mounted to the rotatable wheel. In an embodiment, the aperture 84 allows for the selection of a deuterium lamp located behind the rotatable wheel for absorbance measurements from about 190 nm to about 350 nm.

The excitation filter 42 and the emission filter 62 generally comprise any mechanism for altering the spectrum of light that passes through. Spectrum refers to the wavelength composition of light. A spectral filter may be used to convert white or multichromatic light, which includes light of many colors, into red, blue, green, or other substantially monochromatic light, which includes light of one or only a few colors. The excitation filter 42 and the emission filter 62, preferentially transmit light of preselected wavelengths and preferentially absorb light of other wavelengths.

For convenience, excitation filters may be housed in an excitation filter wheel, which allows the spectrum of excitation light to be changed by rotating a preselected excitation filter into the optical path. Likewise, emission filters may be housed in an emission filter wheel, which allows the spectrum of emission light to be changed by rotating a preselected emission filter into the optical path.

For convenience, excitation filters may be housed in a moveable slide, which allows the spectrum of excitation light to be changed by sliding a preselected excitation filter into the optical path. Likewise, emission filters may be housed in a moveable slide, which allows the spectrum of excitation light to be changed by sliding a preselected emission filter into the optical path.

Spectral filters also may separate light spatially by wavelength. Examples include gratings, monochromators, and prisms. Spectral filters are not required for monochromatic ("single color") light sources, such as certain lasers, which output light of only a single wavelength. Therefore, the excitation filter wheel or slide may include a blank station that does not affect light passage.

Light is transmitted through the fiber optic cable 78 much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. In an alternative embodiment, a short liquid waveguide with low background fluorescence may be used instead of the fiber optic bundle 78.

The polarization filters 48, 72 generally comprise any mechanism for altering the polarization of light. The polarization filters may include an s-polarizer S that passes only s-polarized light, a p-polarizer P that passes only p-polarized light, and a blank O that passes substantially all light, where polarizations are measured relative to the beam splitter. Polarizer filters also may include a standard or ferro-electric liquid crystal display (LCD) polarization switching system. Such a system may be faster than a mechanical switcher. Polarizers also may include a continuous mode LCD polarization rotator with synchronous detection to increase the signal-to-noise ratio in polarization assays. Polarizers may be incorporated as an inherent component in some light sources, such as certain lasers, that intrinsically produce polarized light. Polarizers may also be added excitation filters in an excitation filter wheel or slide for selective use. Likewise, polarizers may be added to emission filters in an emission filter wheel or slide for selective use.

The collection/coupling lenses generally comprise any mechanism for focusing light into a "sensed volume." Apertures may be implemented directly, as an aperture, or indirectly, as the end of a fiber optic cable. Preferred apertures have diameters of 1 mm and 1.5 mm. Lenses and apertures can be used so that only a preselected or sensed volume of the sample is illuminated. The area of illumination will have a diameter corresponding to the diameter of the excitation aperture.

The first and second beam splitters are used to direct excitation or incident light toward the sample and light monitor, and to direct light leaving the sample toward the detector. The beam splitters are changeable, and may be optimized for different assay modes or samples. In some embodiments, switching between beam splitters may be performed manually, whereas in other embodiments, such switching may be performed automatically. Automatic switching may be performed based on direct operator command, or based on an analysis of the sample by the instrument. If a large number or variety of photoactive molecules are to be studied, the beam splitter must be able to accommodate light of many wavelengths; in this case, a "50:50" beam splitter that reflects half and transmits half of the incident light independent of wavelength is optimal. Such a beam splitter can be used with many types of molecules, while still delivering considerable excitation light onto the sample, and while still transmitting considerable light leaving the sample to the detector. If one or a few related photoactive molecules are to be studied, the beam splitter needs only to be able to accommodate light at a limited number of wavelengths; in this case, a "dichroic" or "multidichroic" beam splitter is optimal. Such a beam splitter can be designed with cutoff wavelengths for the appropriate sets of molecules and will reflect most or substantially all of the excitation and background light, while transmitting most or substantially all of the emission light in the case of luminescence. This is possible because the beam splitter may have a reflectivity and transmissivity that varies with wavelength.

The beam splitter more generally comprises any optical device for dividing a beam of light into two or more separate beams. A simple beam splitter (such as a 50:50 beam splitter) may include a very thin sheet of glass inserted in the beam at an angle, so that a portion of the beam is transmitted in a first direction and a portion of the beam is reflected in a different second direction. A more sophisticated beam splitter (such as a dichroic or multi-dichroic beam splitter) may include other prismatic materials, such as fused silica or quartz, and may be coated with a metallic or dielectric layer having the desired transmission and reflection properties, including dichroic and multi-dichroic transmission and reflection properties. In some beam splitters, two right-angle prisms are cemented together at their hypotenuse faces, and a suitable coating is included on one of the cemented faces.

The sample may be anything capable of being measured using optical spectroscopy. The sample can include compounds, mixtures, surfaces, solutions, emulsions, suspensions, cell cultures, fermentation cultures, cells, tissues, secretions, and/or derivatives and/or extracts thereof. Analysis of the sample may involve measuring the presence, concentration, or physical properties (including interactions) of a photoactive analyte in such a sample. Sample may refer to the contents of a single microplate well, or several microplate wells, depending on the assay.

The apparatus may be used with a variety of substrates. As used here, "substrate" generally comprises any material, surface, or other holder capable of supporting a sample for use in optical spectroscopy, and preferably for use with automated sample handling equipment. The substrate may support discrete or continuous samples, where sample sites refer to the locations of discrete samples or the locations of different regions within a continuous sample, respectively. The substrate may support samples at low, intermediate, or high density, and be designed for single or multiple use.

Representative sample holders include microplates, PCR plates, biochips, and chromatography plates, among others. A microplate is a multi-well sample holder, typically but not exclusively used for luminescence applications. A PCR plate is a multi-well sample holder used for performing PCR.

Preferred PCR plates would include a footprint, well spacing, and well shape similar to those of the preferred microplates, while possessing a stiffness adequate for automated handling and a thermal stability adequate for PCR. A biochip is a small, flat surface (such as a glass or silicon wafer, a semiconductor chip, or a multiple-well CCD) onto which biomolecules (such as nucleic acids and proteins) are immobilized in distinct spots or arrays. Biochips include DNA chips, DNA microarrays, gene arrays, and gene chips, among others. As defined here, a chromatography plate is a flat surface used for performing chromatography, electrophoresis, or other separations.

The preferred sample holder is a microplate 424, which includes a plurality of discrete microplate wells 426 for holding samples. Microplates are typically substantially rectangular holders that include a plurality of sample wells for holding a corresponding plurality of samples. These sample wells are normally cylindrical in shape although rectangular or other shaped wells are sometimes used. The sample wells are typically disposed in regular arrays. The "standard" microplate includes 96 cylindrical sample wells disposed in an 8.times.12 rectangular array on 9-millimeter centers. Optionally, microplates having 384 and 1536 sample wells can be used.

The sensed volume generally comprises any volume from which light is detected, and preferably any volume from which light is substantially exclusively detected. The sensed volume may have an hourglass shape, with a cone angle of about 25.degree. and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume.

The combination of top and bottom optics permits assays to combine: (1) top illumination and top detection, or (2) top illumination and bottom detection, or (3) bottom illumination and bottom detection.

Generally, top optics can be used with any sample holder having an open top, whereas bottom optics can be used only with sample holders having optically transparent bottoms, such as glass or thin plastic bottoms. Clear bottom sample holders are particularly suited for measurements involving analytes that accumulate on the bottom of the holder.

Light last passes to a detector, which is used in absorbance, scattering and photoluminescence assays, among others. A preferred detector is a photomultiplier tube (PMT).

More generally, detectors comprise any mechanism capable of converting energy from detected light into signals that may be processed by the apparatus, and by the processor in particular. Suitable detectors include photomultiplier tubes, channel photomultipliers, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others.

Large variations in experimental protocols can be achieved by rotating the wheel of light sources to select a light source 12, moving one of the first and second shutters 56, 58 and by selecting the proper excitation and emission filters 42, 62. Additionally, the rotatable wheel of light sources, the first and second shutters, the excitation filter and polarizer slider, and the emission filter and slider may be coupled to electric motors. The electric motors may be computer controlled.

Figure 2:
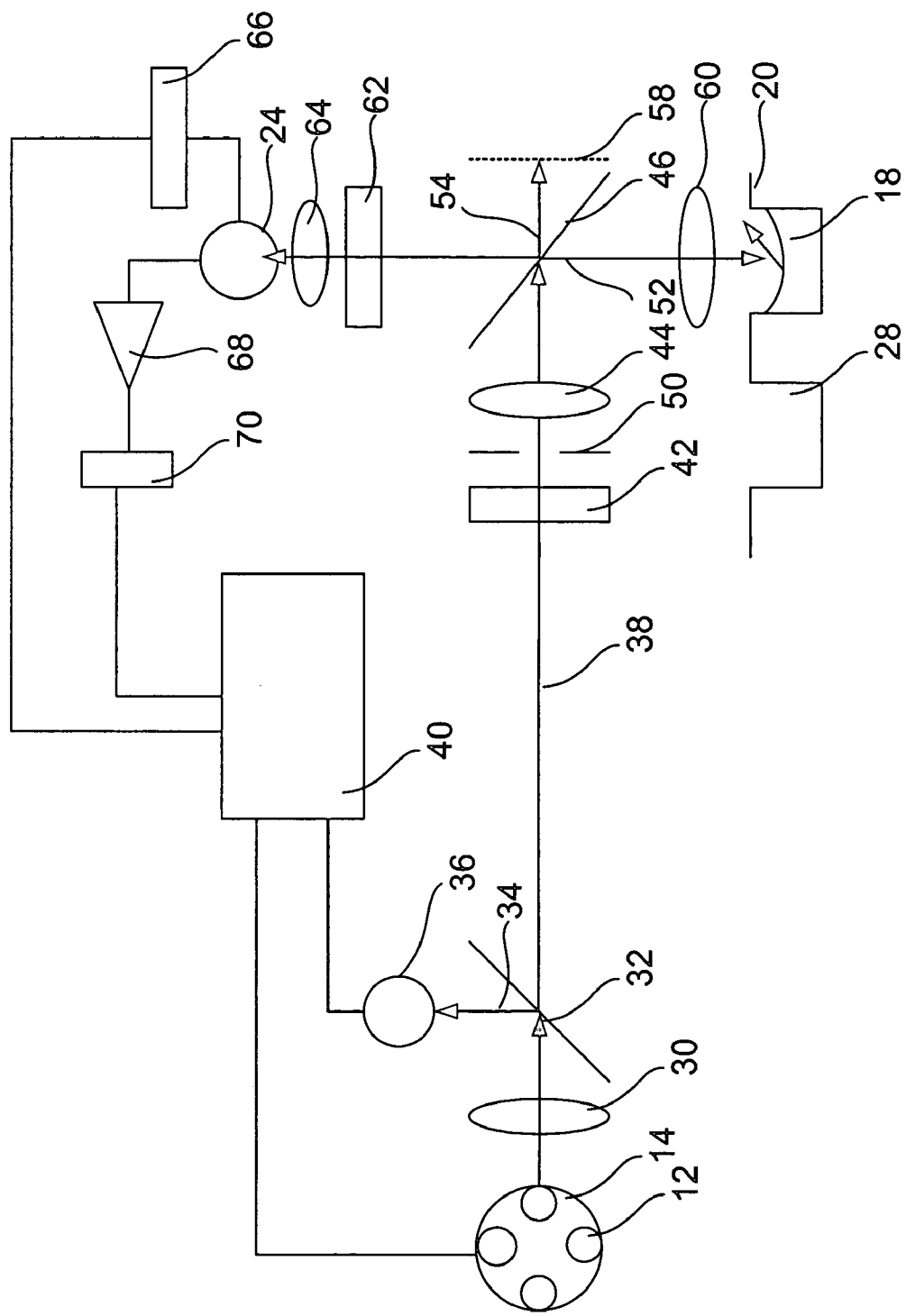
FIG. 2 is a schematic illustration of the apparatus of FIG. 1 configured for measuring fluorescence top intensity and time resolved fluorescence.

As shown in FIG. 2, the apparatus of the present invention can be used for measuring fluorescence top intensity and time resolved fluorescence. As shown in FIG. 2, the second shutter 58 is positioned to block the fourth beam of excitation light 54. The third beam of excitation light 52 is directed onto the top of a sample 18 at a sample site 28 on the substrate 20. Emitted light from the sample passes through the short focal length lens 60 through the second beam splitter 46. The emitted light then passes through the emission filter 62 and the collimating lens 64 and onto the upper detector 24. When measuring time resolved fluorescence, multiple measurements are taken from the upper detector 24 at predetermined time intervals.

Figure 3:
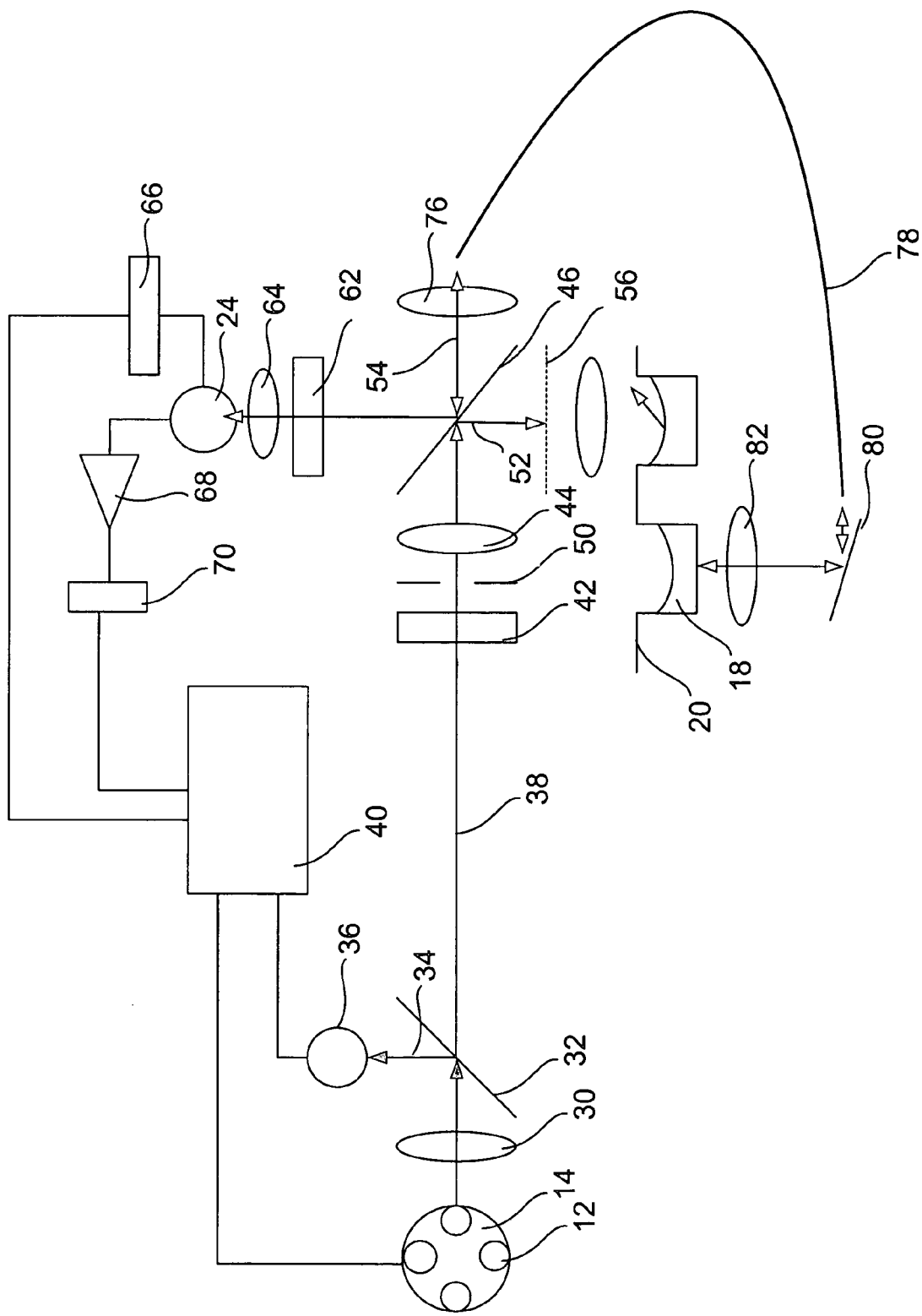
FIG. 3 is a schematic illustration of the apparatus of FIG. 1 configured for measuring bottom fluorescence intensity.

As shown in FIG. 3 the apparatus 10 can be used for measuring bottom fluorescence intensity. As shown in FIG. 3, the first shutter 56 is positioned to block the third beam of excitation light 52. The fourth beam of excitation light 54 is directed onto the bottom of a sample 18 at a sample site 28 on the substrate 20. Emitted light exiting the bottom of the sample 18 passes through the coupling lens 82 and onto the mirror 80. The mirror 80 directs the emitted light into the fiber optic cable 78. The emitted light is then directed through the coupling lens 76 and onto the second beam splitter 46. A portion of the emitted light is directed by the second beam splitter 46 through the emission filter 62 and the lens 64 onto the upper detector 24.

Figure 4:
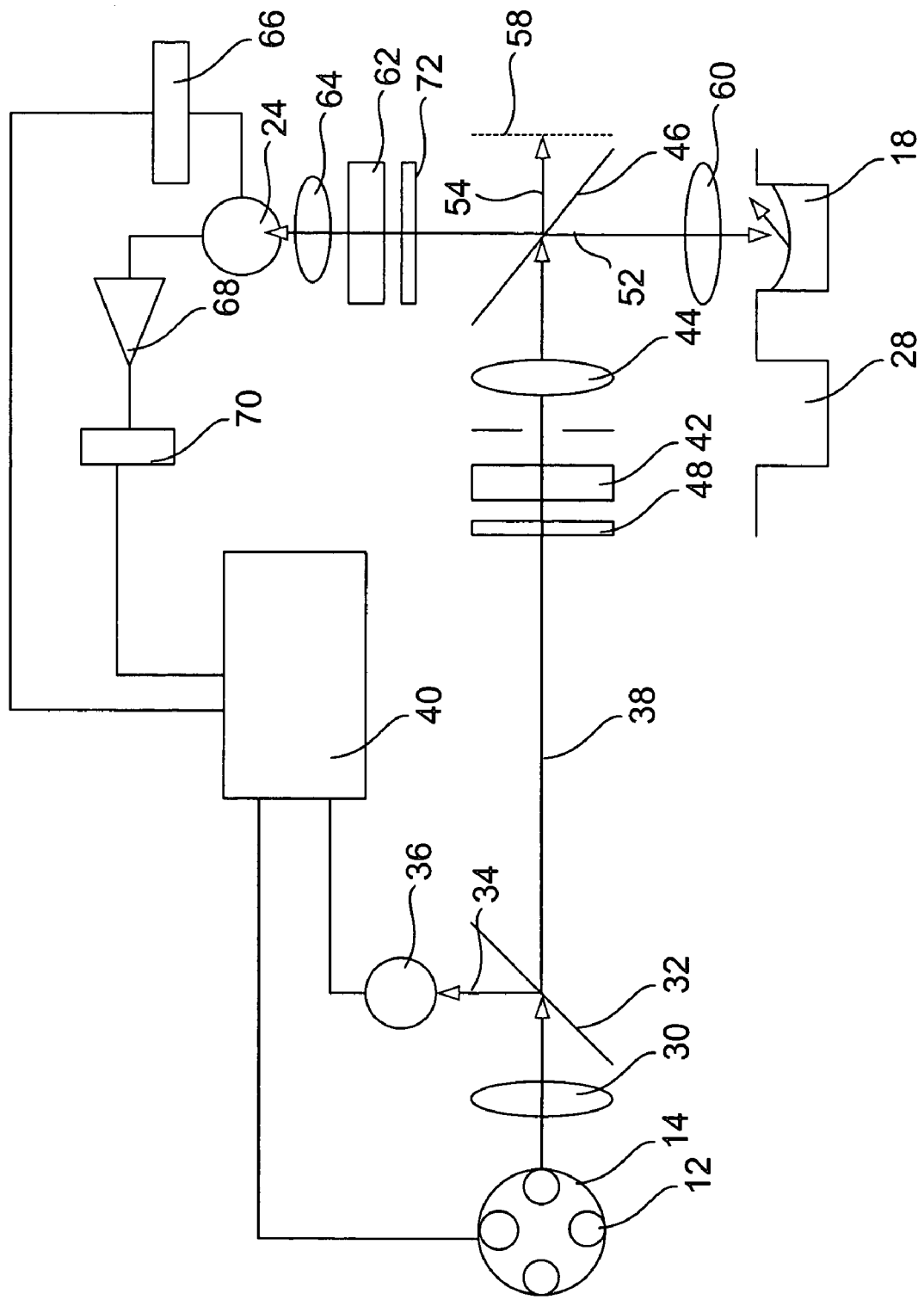
FIG. 4 is a schematic illustration of the apparatus of FIG. 1 configured for measuring fluorescence polarization.

As shown in FIG. 4, the apparatus 10 can be adapted for measuring fluorescence polarization. The second beam of excitation light 38 passes through the beam polarizer 48, the excitation filter 42, the lens 44 and onto the second beam splitter 46. The second beam splitter 46 splits the second beam of excitation light 38 into a third beam of excitation light 52 directed onto a sample 18 at a sample site 28 on the substrate 20, and a fourth beam of excitation light 54. As shown in FIG. 4, the second shutter 58 is positioned to block the fourth beam of excitation light 54.

Light emitted from the top of the sample 18 passes up through the lens 60 and onto the second beam splitter 46. A portion of the emitted light passes through the second beam splitter 46, through the emission polarizer 72, through the emission filter 62, through the lens 64 and onto the upper detector 24 for measurement.

Figure 5:
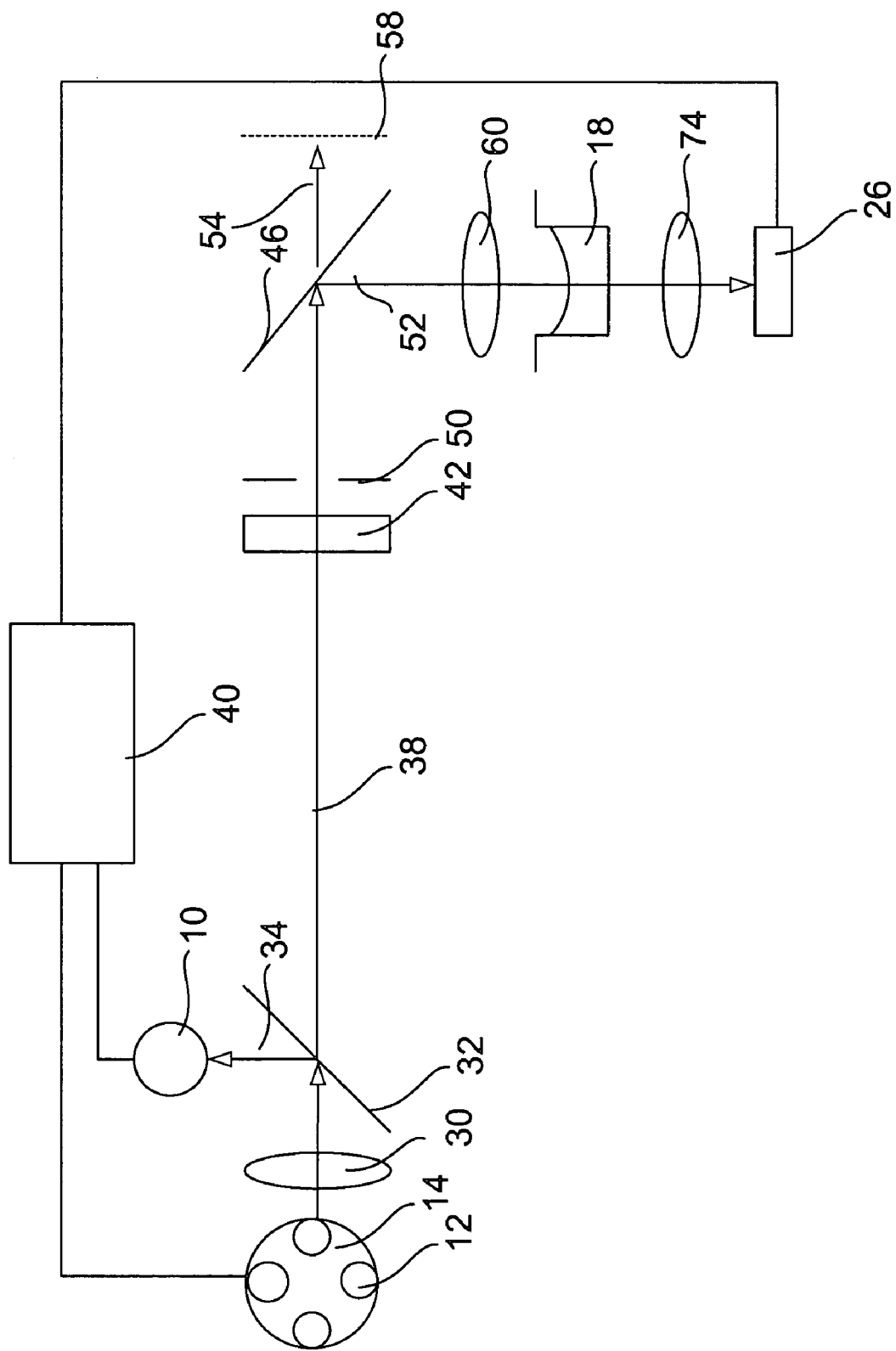
FIG. 5 is a schematic illustration of the apparatus of FIG. 1 configured for measuring absorbance.

As shown in FIG. 5, the apparatus can be adapted for measuring absorbance. As shown in FIG. 5, the second shutter 58 is positioned to block the fourth beam of excitation light 54. The third beam of excitation light 52 is directed onto the top of a sample 18 at a sample site 28 on the substrate 20. Any excitation light not absorbed by the sample 18 passes through the sample 18, through a clear bottom of the substrate 20, through the collimating lens 74 and onto the lower detector 26 for measurement.

Figure 6:
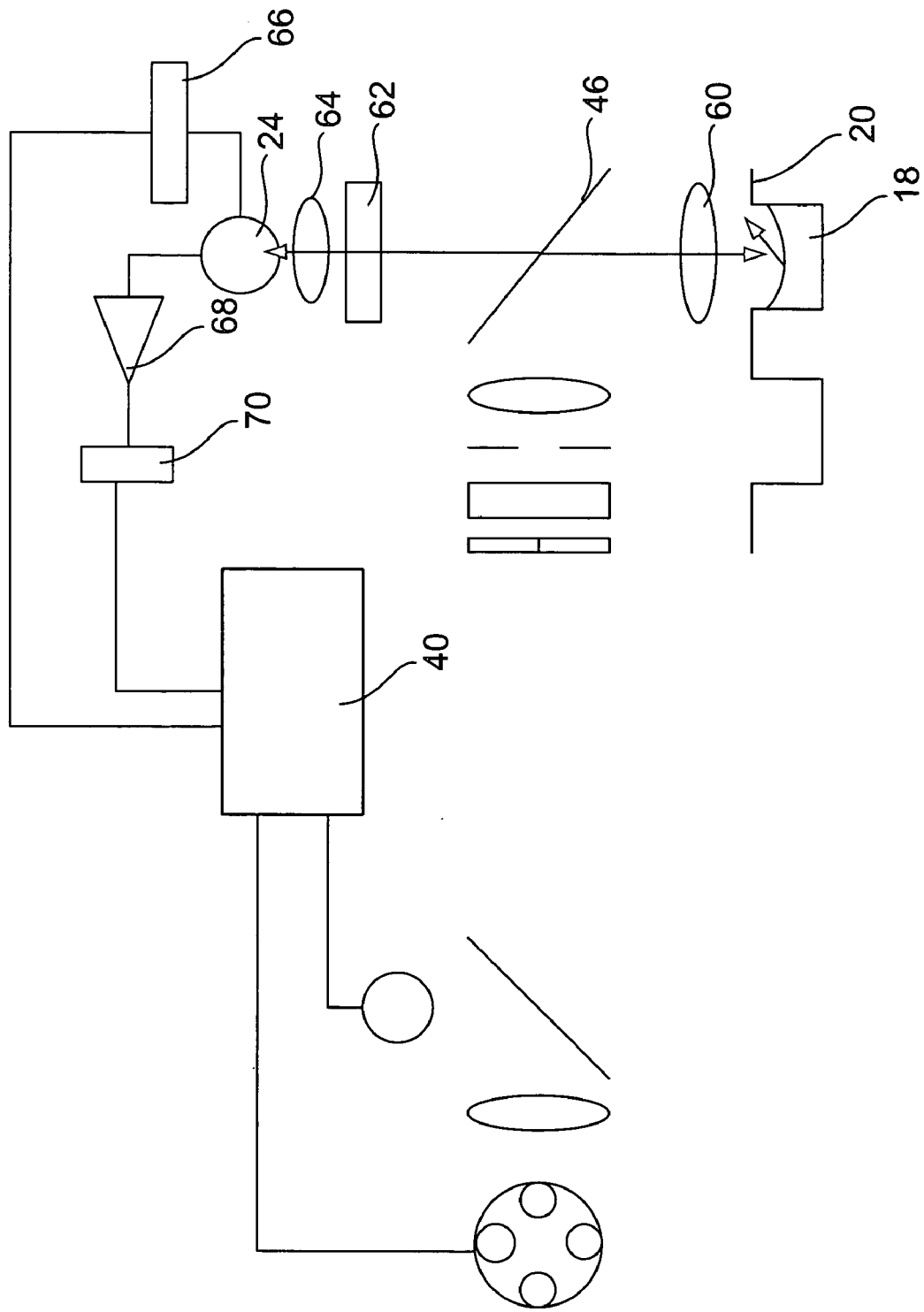
FIG. 6 is a schematic illustration of the apparatus of FIG. 1 configured for measuring luminescence.

As shown in FIG. 6, the apparatus can be adapted for measuring luminescence. In a typical luminescence measurement, no excitation light is transmitted to the sample 18. Rather emission light from the sample 18 passes up through collimating lens 60, second beam splitter 46, emission filter 62, collimating lens 64, and onto the upper detector 24 for measurement.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts and drawings, and all the steps in any method or process disclosed, may be combined in any combination except combination where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

What is claimed is:

1. An apparatus for analyzing a plurality of samples in sample sites on a substrate, the apparatus comprising:
   a) an array of spaced apart light sources coupled to a moveable support so that one or more of the light sources can be selectively used;
   b) a frame for supporting the substrate;
   c) a detector configured to detect light;
   d) an optical relay configured to transmit light from at least one of the light sources to one of the plurality of sample sites and from the sample site to the detector; and
   e) a support structure for supporting the moveable support, the frame, the detector and the optical relay;
   wherein the moveable support is moveable independently of the optical relay.

2. The apparatus of claim 1 further comprising a selection switch coupled to the moveable support.

3. An apparatus for analyzing a plurality of samples in samples sites on a substrate, the apparatus comprising:
   a) an array of spaced apart light sources coupled to a moveable support so that one or more of the light sources can be selectively used;
   b) a frame for supporting the substrate;
   c) a detector configured to detect light;
   d) an optical relay configured to transmit light from at least one of the light sources to one of the plurality of sample sites and from the sample site to the detector; and
   e) a support structure for supporting the frame, the detector and the optical relay;
   wherein the frame is configured to move the substrate in a first direction so that the sample sites pass sequentially through an examination region.

4. An apparatus for analyzing a plurality of samples in samples sites on a substrate, the apparatus comprising:
   a) an array of spaced apart light sources coupled to a moveable support so that one or more of the light sources can be selectively used;
   b) a frame for supporting the substrate;
   c) a detector configured to detect light;
   d) an optical relay configured to transmit light from at least one of the light sources to one of the plurality of sample sites and from the sample site to the detector; and
   e) a support structure for supporting the frame, the detector and the optical relay;
   wherein the moveable support is a rotatable wheel.

5. An apparatus for analyzing a plurality of samples in samples sites on a substrate, the apparatus comprising:
   a) an array of spaced apart light sources coupled to a moveable support so that one or more of the light sources can be selectively used;
   b) a frame for supporting the substrate;
   c) a detector configured to detect light;
   d) an optical relay configured to transmit light from at least one of the light sources to one of the plurality of sample sites and from the sample site to the detector; and
   e) a support structure for supporting the frame, the detector and the optical relay;
   wherein the moveable support further comprises an aperture for the passage of light from an exterior light source not positioned on the moveable support.

6. The apparatus of claim 5 wherein the exterior light source is a deuterium lamp.

7. The apparatus of claim 1 wherein the array of light sources further comprises at least one LED lamp.

8. The apparatus of claim 1 wherein the array of light sources further comprises a plurality of LED lamps, each of the plurality of LED lamps emitting light at a wavelength different than the others of the plurality of LED lamps.

9. The apparatus of claim 1 wherein the array of light sources further comprises:
   an LED lamp having a wavelength range from about 450 nm to about 705 nm; and
   an LED lamp having a wavelength centered at about one of 370, 430, 470, 590, 620, 910 and 960 nm.

10. An apparatus for analyzing a plurality of samples in sample sites on a substrate, the apparatus comprising:
    a) an array of spaced apart light sources coupled to a moveable support so that one or more of the light sources can be selectively used;
    b) a frame for supporting the substrate;
    c) a detector configured to detect light;
    d) an optical relay configured to transmit light from at least one light source to one of the sample sites on the substrate and from the sample site to the detector; and
    e) a support structure for supporting the stage, the detector and the optical relay;
    wherein the optical relay further comprises a beam splitter for splitting light from at least one of the array of light sources into two beams, a first beam being directed to an upper surface of the sample site, and a second beam directed to a lower surface of the sample site.

11. The apparatus of claim 10 wherein the second beam is directed to a lower surface of the sample site by a fiber optic cable.

12. The apparatus of claim 10 wherein the second beam is directed to a lower surface of the sample site by a liquid waveguide.

13. The apparatus of claim 10 wherein the optical relay further comprises a first shutter selectively moveable to prevent light from the beam splitter from reaching the upper surface of the sample site.

14. The apparatus of claim 13 wherein the optical relay further comprises a second shutter selectively moveable to prevent light from the beam splitter from reaching the lower surface of the sample site.

15. The apparatus of claim 14 wherein the first and second shutter further comprise anodized steel.

16. The apparatus of claim 10 wherein the optical relay further comprises at least one of a first shutter selectively moveable to prevent light from the beam splitter from reaching the upper surface of the sample site and a second shutter selectively moveable to prevent light from the beam splitter from reaching the lower surface of the sample site.

17. An apparatus for analyzing a plurality of samples in sample sites on a substrate, the apparatus comprising:
   a) an array of spaced apart light sources coupled to a moveable support so that one or more of the light sources can be selectively used;
   b) a frame for supporting the substrate;
   c) a detector configured to detect light;
   d) an optical relay configured to transmit light from at least one light source to one of the sample sites on the substrate and from the sample site to the detector; and
   e) a support structure for supporting the stage, the detector and the optical relay;
   wherein the optical relay further comprises:
      a beam splitter for splitting light from at least one of the array of light sources into two beams, a first beam being directed to an upper surface of the sample site, and a second beam directed to a lower surface of the sample site; and
      a means for blocking at least one of the first beam and the second beam.

18. A method for analyzing a sample, comprising:
selecting the apparatus of claim 1;
placing a sample at the sample site on the substrate;
selecting a light source; and
detecting emission light from the sample.

19. An apparatus for analyzing a plurality of samples in sample sites on substrate, the apparatus comprising:
   a) an array of spaced apart light sources coupled to a rotatable wheel so that one or more of the light sources can be selectively used;
   b) a frame for supporting the substrate;
   c) a detector configured to detect light;
   d) an optical relay configured to transmit light from at least one light source to one of the sample sites on the substrate and from the sample site to the detector, the optical relay further comprising:
      a beam splitter for splitting light from at least one of the array of light sources two beams, a first beam being directed to an upper surface of the sample site, and a second beam directed to a lower surface of the sample site; and
      a first shutter selectively moveable to block the first beam; and
      a second shutter selectively moveable to block the second beam; and
   e) a support structure for supporting the stage, the detector and the optical relay; and
   wherein at least one of the light sources is an LED.

20. A method for analyzing a sample, comprising:
selecting the apparatus of claim 17;
placing a sample at the sample site on the substrate;
selecting a light source; and
detecting emission light from the sample.

* * * * *